United States Patent
Nihonyanagi et al.

(10) Patent No.: US 12,380,731 B2
(45) Date of Patent: Aug. 5, 2025

(54) INFORMATION PROCESSING DEVICE, AND EMOTION ESTIMATION METHOD

(71) Applicant: Mitsubishi Electric Corporation, Tokyo (JP)

(72) Inventors: Sakiko Nihonyanagi, Tokyo (JP); Keigo Kawashima, Tokyo (JP); Shu Murayama, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 426 days.

(21) Appl. No.: 17/894,289

(22) Filed: Aug. 24, 2022

(65) Prior Publication Data
US 2022/0415086 A1 Dec. 29, 2022

Related U.S. Application Data

(63) Continuation of application No. PCT/JP2020/019906, filed on May 20, 2020.

(51) Int. Cl.
*G06V 40/16* (2022.01)
*G06F 21/32* (2013.01)

(52) U.S. Cl.
CPC ............ *G06V 40/174* (2022.01); *G06F 21/32* (2013.01); *G06V 40/161* (2022.01)

(58) Field of Classification Search
CPC .. G06V 40/174; G06V 40/161; G06V 40/193; G06V 20/53; G06V 40/176;
(Continued)

(56) References Cited

U.S. PATENT DOCUMENTS

| 2005/0264425 A1* | 12/2005 | Sato ........................ G08B 31/00 340/506 |
| 2010/0086204 A1* | 4/2010 | Lessing ................... G06F 16/58 382/165 |

(Continued)

FOREIGN PATENT DOCUMENTS

| JP | 6-251273 A | 9/1994 |
| JP | 2005-348872 A | 12/2005 |

(Continued)

OTHER PUBLICATIONS

International Search Report, issued in PCT/JP2020/019906, PCT/ISA/210, dated Jul. 28, 2020.
(Continued)

*Primary Examiner* — Nimesh Patel
(74) *Attorney, Agent, or Firm* — Birch, Stewart, Kolasch & Birch, LLP

(57) ABSTRACT

An information processing device includes an acquisition unit, an identification unit and an emotion estimation unit. The acquisition unit acquires input information as information regarding a user in a certain situation. The identification unit identifies an object to which the user is paying attention and the user's appearance when the user is paying attention to the object based on the input information. The emotion estimation unit estimates emotion of the user based on object information indicating the identified object, appearance information indicating the identified appearance, and a predetermined method of estimating the emotion.

28 Claims, 13 Drawing Sheets

(58) Field of Classification Search
CPC ...... G06V 40/172; G06V 20/52; G06V 20/80;
G06V 40/20; G06V 10/82; G06V 40/16;
G06V 40/166; G06V 40/10; G06V
40/103; G06V 40/70; G06V 40/168;
G06F 21/32; G06F 3/147; G06F 3/011;
G06F 16/00; G06F 3/0481; G06F
2203/011; G06F 11/3438; G06F
2209/5021; G06F 1/1605; G06F 15/16;
G06F 16/24578; G06F 16/284; G06F
16/436; G06F 3/017; G06F 3/0237; A61B
5/16; G06T 7/00; G06T 7/70; H04L
67/535; H04L 43/0817; H04L 51/10;
H04L 67/025; H04L 41/16; H04L
25/0224; H04L 25/0226
See application file for complete search history.

(56) References Cited

U.S. PATENT DOCUMENTS

| | | | | |
|---|---|---|---|---|
| 2012/0120219 A1* | 5/2012 | Wang | .................. | H04N 21/4223 382/128 |
| 2013/0243270 A1* | 9/2013 | Kamhi | .................. | H04N 21/458 382/118 |
| 2017/0102765 A1* | 4/2017 | Yoneda | .............. | G06Q 30/0269 |
| 2017/0362054 A1* | 12/2017 | Légeret | .................. | G06V 40/174 |
| 2020/0250498 A1* | 8/2020 | Kazi | .......................... | G06T 1/00 |
| 2021/0103941 A1* | 4/2021 | Patil | ..................... | G06V 40/161 |

FOREIGN PATENT DOCUMENTS

| | | |
|---|---|---|
| JP | 2017-201499 A | 11/2017 |
| JP | 2019-47234 A | 3/2019 |
| JP | 2019-101775 A | 6/2019 |

OTHER PUBLICATIONS

Written Opinion of the International Searching Authority, issued in PCT/JP2020/019906, PCT/ISA/237, dated Jul. 28, 2020.

* cited by examiner

FIG. 4

| FRAME NUMBER | ATTENTION TARGET | ATTENTION FREQUENCY | POSTURE | HEART RATE |
|---|---|---|---|---|
| $t_1$ | FLOOR NUMBER DISPLAY | 0.8 | CROSSED ARMS | 80 |
| $t_2$ | ELEVATOR DOOR | 0.5 | STANDING STRAIGHT | 75 |
| $t_3$ | CALL BUTTON | 0.1 | STANDING STRAIGHT | 70 |
| ... | ... | ... | ... | ... |

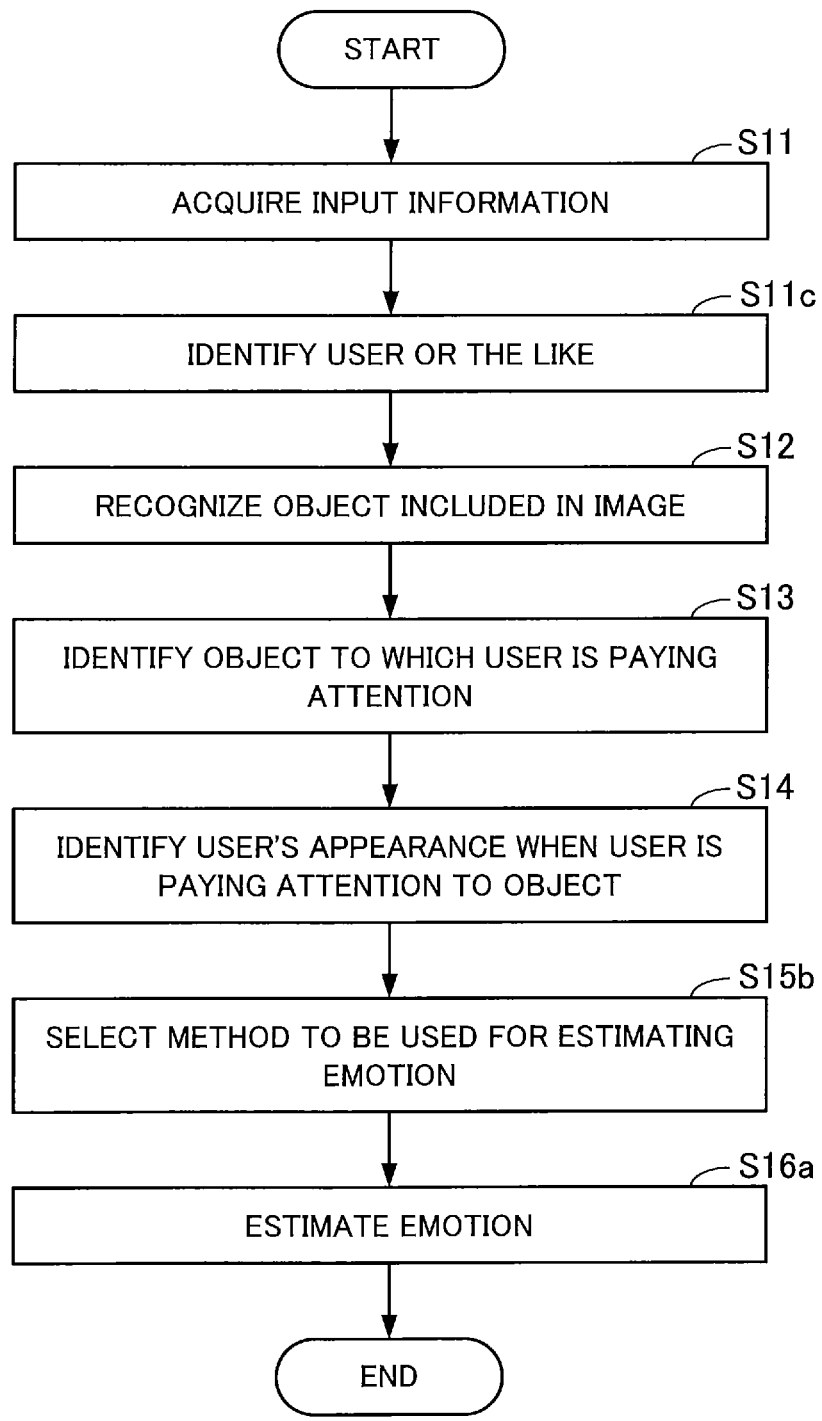

FIG. 13

| FRAME NUMBER | ATTENTION TARGET | ATTENTION FREQUENCY | POSTURE | HEART RATE | USER | TYPE |
|---|---|---|---|---|---|---|
| $t_1$ | FLOOR NUMBER DISPLAY | 0.8 | CROSSED ARMS | 80 | $Usr_1$ | SHORT-TEMPERED |
| $t_2$ | ELEVATOR DOOR | 0.5 | STANDING STRAIGHT | 75 | | |
| $t_3$ | CALL BUTTON | 0.1 | STANDING STRAIGHT | 70 | | |
| ... | ... | ... | ... | ... | | |

METHOD TABLE 111

| METHOD ID | ATTENTION TARGET | CONDITION 1 ATTENTION FREQUENCY | CONDITION 2 POSTURE | CONDITION 3 HEART RATE | CONDITION 4 USER | CONDITION 5 TYPE | METHOD WEIGHT OF EMOTION |
|---|---|---|---|---|---|---|---|
| $id_1$ | FLOOR NUMBER DISPLAY | ≥ 0.8 | CROSSED ARMS | ≥ 80 | $Usr_1$ | SHORT-TEMPERED | IRRITATION: 1.5 |
| $id_2$ | FLOOR NUMBER DISPLAY | ≥ 0.5 | CROSSED LEGS | ≥ 70 | $Usr_1$ | NORMAL | IRRITATION: 1.2 |
| $id_3$ | FLOOR NUMBER DISPLAY | ≥ 0.1 | STANDING STRAIGHT | ≥ 60 | $Usr_1$ | PATIENT | IRRITATION: 0 |
| ... | ... | ... | ... | ... | ... | ... | ... |

INFORMATION PROCESSING DEVICE, AND EMOTION ESTIMATION METHOD

CROSS-REFERENCE TO RELATED APPLICATION

This application is a continuation application of International Application No. PCT/JP2020/019906 having an international filing date of May 20, 2020.

BACKGROUND OF THE INVENTION

1. Field of the Invention

The present disclosure relates to an information processing device, and an emotion estimation method.

2. Description of the Related Art

Behavior of a user can be identified based on biological information, voice information, an image, sight line data or the like. Further, emotion of a user using equipment can be estimated based on information indicating the behavior of the user. Here, a technology for estimating the emotion has been proposed (see Patent Reference 1). An information processing device described in the Patent Reference 1 estimates the emotion of a photographer based on sight line data regarding the photographer and sensor data regarding the photographer.

The equipment executes a response or a process corresponding to the estimated emotion. For example, the emotion of a user situated in front of an elevator is identified. When the user is irritated, the equipment executes a process for reducing the irritation.

Patent Reference 1: Japanese Patent Application Publication No. 2019-47234

Incidentally, it is possible to employ a method of estimating the emotion of a user based on the user's state when the user is paying attention. However, the user's emotion when the user is paying attention is not constant. For example, the user's emotion when the user is paying attention to a pedestrian in the background of a subject and the user's emotion when the user is paying attention to the subject as the target of the photographing are different from each other. As above, estimating that the user's emotion when the user is paying attention is constantly the same is a mistake.

SUMMARY OF THE INVENTION

An object of the present disclosure is to increase the estimation accuracy of the emotion.

An information processing device according to an aspect of the present disclosure is provided. The information processing device includes an acquisition unit that acquires input information as information regarding a user in a certain situation, an identification unit that identifies an object to which the user is paying attention and the user's appearance when the user is paying attention to the object based on the input information and an emotion estimation unit that estimates emotion of the user based on object information indicating the identified object, appearance information indicating the identified appearance, and a predetermined method of estimating the emotion.

According to the present disclosure, the estimation accuracy of the emotion can be increased.

BRIEF DESCRIPTION OF THE DRAWINGS

The present disclosure will become more fully understood from the detailed description given hereinbelow and the accompanying drawings which are given by way of illustration only, and thus are not limitative of the present disclosure, and wherein:

FIG. 4 is a diagram showing examples of attention relevant information in the first embodiment;

FIG. 12 is a flowchart showing an example of a process executed by the information processing device in the fourth embodiment; and FIG. 13 is a diagram showing an example of a method table in the fourth embodiment.

DETAILED DESCRIPTION OF THE INVENTION

Embodiments will be described below with reference to the drawings. The following embodiments are just examples and a variety of modifications are possible within the scope of the present disclosure.

First Embodiment

Figure 1:
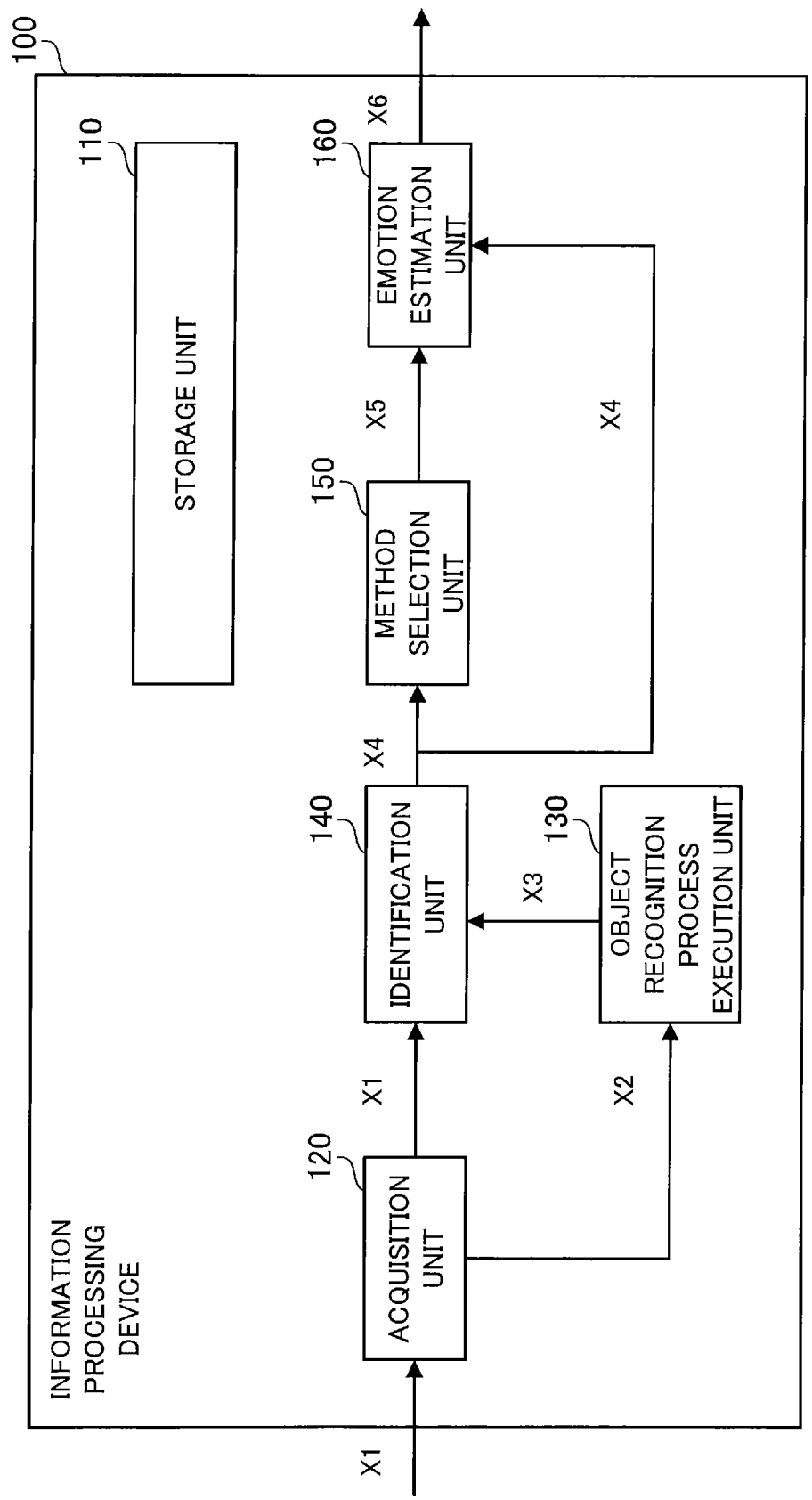
FIG. 1 is a diagram showing functional blocks included in an information processing device in a first embodiment.

FIG. 1 is a diagram showing functional blocks included in an information processing device in a first embodiment. An information processing device 100 is a device that executes an emotion estimation method. The information processing device 100 may be referred to also as an "emotion estimation device".

Here, hardware included in the information processing device 100 will be described below.

Figure 2:
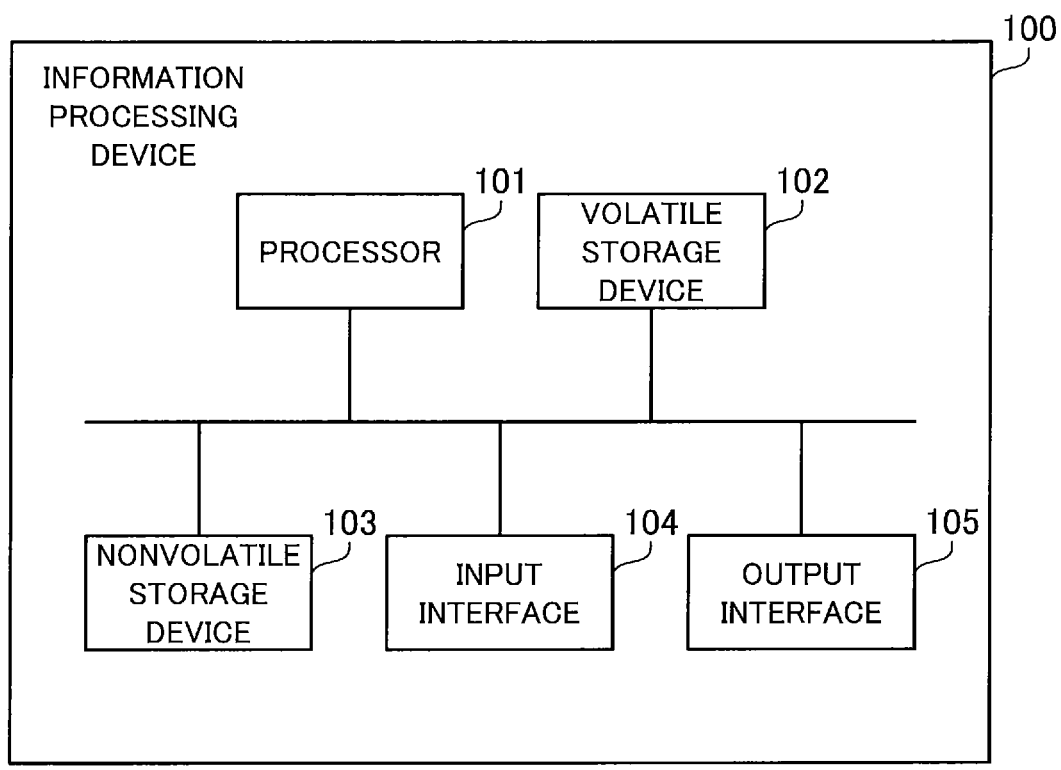
FIG. 2 is a diagram showing the configuration of hardware included in the information processing device in the first embodiment.

FIG. 2 is a diagram showing the configuration of the hardware included in the information processing device in the first embodiment. The information processing device 100 includes a processor 101, a volatile storage device 102, a nonvolatile storage device 103, an input interface 104 and an output interface 105.

The processor 101 controls the whole of the information processing device 100. For example, the processor 101 is a Central Processing Unit (CPU), a Field Programmable Gate Array (FPGA) or the like. The processor 101 can also be a multiprocessor. The information processing device 100 may include a processing circuitry instead of the processor 101. The processing circuitry may be either a single circuit or a combined circuit.

The volatile storage device 102 is main storage of the information processing device 100. The volatile storage device 102 is a Random Access Memory (RAM), for example. The nonvolatile storage device 103 is auxiliary storage of the information processing device 100. The nonvolatile storage device 103 is a Hard Disk Drive (HDD) or a Solid State Drive (SSD), for example.

The input interface 104 acquires input information from the outside. The input information will be described later. The output interface 105 outputs information to an external device connectable to the information processing device 100.

Returning to FIG. 1, functions of the information processing device 100 will be described below.

The information processing device 100 includes a storage unit 110, an acquisition unit 120, an object recognition process execution unit 130, an identification unit 140, a method selection unit 150 and an emotion estimation unit 160.

The storage unit 110 may be implemented as a storage area reserved in the volatile storage device 102 or the nonvolatile storage device 103.

Part or all of the acquisition unit 120, the object recognition process execution unit 130, the identification unit 140, the method selection unit 150 and the emotion estimation unit 160 may be implemented by a processing circuitry. Part or all of the acquisition unit 120, the object recognition process execution unit 130, the identification unit 140, the method selection unit 150 and the emotion estimation unit 160 may be implemented as modules of a program executed by the processor 101. For example, the program executed by the processor 101 is referred to also as an "emotion estimation program". The emotion estimation program has been recorded in a record medium, for example.

The storage unit 110 may store a method table. A plurality of methods have been registered in the method table. Each of the plurality of methods is a method of estimating the emotion. Here, the method table is referred to also as method information.

The acquisition unit 120 acquires input information X1. The input information X1 is information regarding a user in a certain situation. The input information X1 can also be information regarding a user in a certain situation at a certain time point. For example, the certain situation can be a situation where the user is waiting for an elevator, a situation where the user is driving a vehicle, or the like. Further, the input information X1 may also be represented as information regarding behavior of a user. Specifically, the input information X1 includes an image X2, voice information indicating voice of the user, biological information on the user, sight line data, motion information, or the like. Incidentally, the input information X1 may also be configured to include at least the image X2. Parenthetically, the input information X1 may be referred to also as sensor information.

The biological information included in the input information X1 can be acquired by using a noncontact sensor or a contact sensor. The noncontact sensor is a camera, a thermography camera or an expiration sensor, for example. When the noncontact sensor is a camera, biological information such as heartbeat or pulsation is acquired based on blood flow information on the facial surface included in images acquired from the camera. When the noncontact sensor is a thermography camera, biological information indicating body temperature is acquired based on thermography. When the noncontact sensor is an expiration sensor, biological information as information regarding the expiration is acquired from the expiration sensor. The contact sensor is a wearable device such as a smartwatch, for example. Biological information such as the heartbeat, the pulsation or perspiration is acquired from the wearable device. When the contact sensor is embedded in a steering wheel or a seat belt, the heartbeat and the pulsation are acquired from the contact sensor as the biological information.

The sight line data included in the input information X1 is data indicating the user's attention position in the image X2. For example, the sight line data is acquired from an eye tracking sensor.

The motion information included in the input information X1 is information indicating motion of the user. The motion information is acquired by means of motion capture. Further, the motion information is acquired from Kinect (registered trademark) of Microsoft (registered trademark).

The object recognition process execution unit 130 executes a process of recognizing an object included in the image X2.

The identification unit 140 identifies an object to which the user is paying attention and the user's appearance when the user is paying attention to the object based on the input information X1. Further, the identification unit 140 may identify the object to which the user is paying attention based on information obtained by the process and the input information X1.

Based on object information indicating the identified object, appearance information indicating the identified appearance, and the method table, the method selection unit 150 selects a method corresponding to the object information and the appearance information from the plurality of methods.

The emotion estimation unit 160 estimates the emotion of the user based on the selected method, the object information and the appearance information.

Next, a process executed by the information processing device 100 will be described below by using a flowchart.

Figure 3:
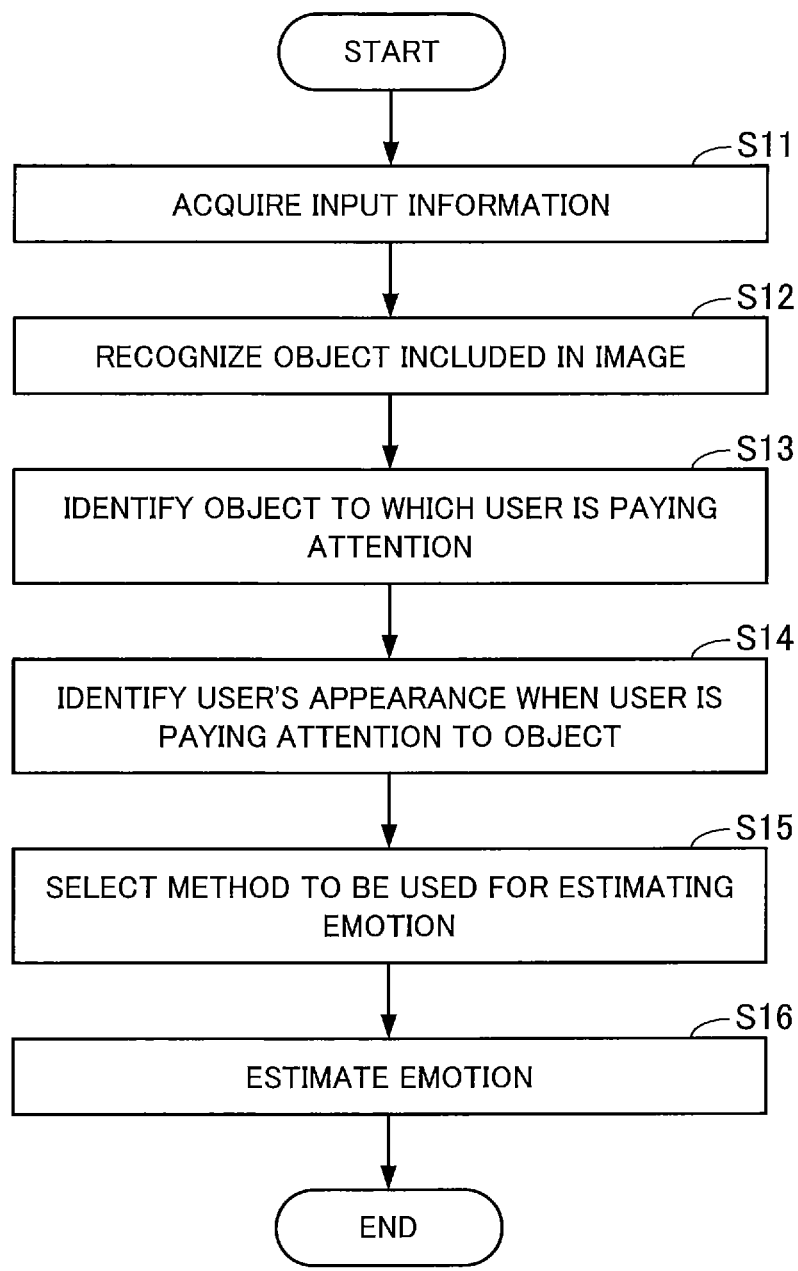
FIG. 3 is a flowchart showing an example of a process executed by the information processing device in the first embodiment.

FIG. 3 is a flowchart showing an example of the process executed by the information processing device in the first embodiment.

(Step S11) The acquisition unit 120 acquires the input information X1.

(Step S12) The object recognition process execution unit 130 acquires the image X2 included in the input information X1. The image X2 is an image obtained by photographing the user's vicinity. Incidentally, the image X2 is desired to include the object to which the user is paying attention as will be described later. Thus, it is permissible even if the image X2 does not include the user. Accordingly, the vicinity may be regarded as a place separate from the user or a range including the user.

The object recognition process execution unit 130 executes a process of recognizing an object included in the image X2. For example, generic object recognition or specific object recognition is used in the process. A processing result X3 is obtained by executing the process. Namely, the processing result X3 is information obtained by the process.

For example, the processing result X3 indicates a part of equipment operated by the user. In the case of an elevator, for example, the part is a call button, an elevator door, a floor number display or a floor. In the case of a vehicle, the part is a navigation screen or a window. Further, for example, the processing result X3 indicates the user's body part. The body part is a toe, for example. Furthermore, for example, the processing result X3 is an article worn by the user, an article possessed by the user, or the like. The article worn by the user is a watch, for example. The article possessed by the user is a smartphone, for example.

Further, an identifier (ID) may be associated with the object (specifically, a name of the object) indicated by the processing result X3. Furthermore, information indicating a position in the image X2 may be associated with the object indicated by the processing result X3. Incidentally, the information indicating the position is represented by coordinates. Moreover, the processing result X3 can include region information indicating a range of the identified object in the image X2.

Further, the object recognition process execution unit 130 may acquire a plurality of images. For example, the plurality of images are images obtained by photographing the user situated in an elevator hall every second for 30 seconds. The object recognition process execution unit 130 executes a process of recognizing an object included in each of the plurality of images. Namely, the object recognition process execution unit 130 executes a process of recognizing an object for each image. By this process, sequential processing results are obtained. For example, sequential 30 processing results based on 30 images are obtained.

(Step S13) The identification unit 140 identifies the object to which the user is paying attention. The identification process will be described in detail below.

The identification unit 140 identifies the object to which the user is paying attention based on the processing result X3 and the image X2 including the user. Specifically, based on the image X2, the identification unit 140 identifies the user's face direction, the user's body direction, a peculiar motion when the user is paying attention to the object, the user's posture, or the like. Incidentally, the identification unit 140 is capable of identifying the user's face direction, the user's body direction, the peculiar motion, the user's posture, or the like by using a publicly known technology. The identification unit 140 identifies the object to which the user is paying attention based on the identified information and the processing result X3. The identification process will be described specifically below.

In the case where the user's face direction has been identified, the identification unit 140 identifies an object situated in the user's face direction as the object to which the user is paying attention based on the processing result X3.

The case where the peculiar motion has been identified will be described below. For example, the peculiar motion is a motion of looking at a wrist watch, a motion of looking at a smartphone, or the like. In the case where the motion of looking at a wrist watch has been identified, the identification unit 140 identifies the wrist watch to which the user is paying attention based on the processing result X3.

For example, in the case where the user's posture has been identified, the identification unit 140 identifies the object to which the user is paying attention based on a neck inclination and an arm position indicated by the user's posture and the processing result X3. Specifically, when the user's posture indicates that "an arm is raised and the face is pointed obliquely sideways", the identification unit 140 identifies a wrist watch from the processing result X3.

When the sight line data is included in the input information X1, the identification unit 140 identifies the object to which the user is paying attention based on the sight line data and the processing result X3. Specifically, when information indicating a position in the image X2 has been associated with the object indicated by the processing result X3, the identification unit 140 identifies the object to which the user is paying attention based on the position of the object indicated by the processing result X3 and the user's attention position indicated by the sight line data.

When the voice information is included in the input information X1, the identification unit 140 identifies the object to which the user is paying attention based on the voice information. Specifically, the identification unit 140 analyzes the contents of the user's speech indicated by the voice information and identifies the object to which the user is paying attention based on the result of the analysis.

For example, when the motion information is included in the input information X1, the identification unit 140 identifies the object to which the user is paying attention based on the user's neck direction or body direction indicated by the motion information and the processing result X3.

(Step S14) The identification unit 140 identifies the user's appearance when the user is paying attention to the object based on the input information X1. In other words, the identification unit 140 identifies the state when the user is paying attention to the object based on the input information X1. Here, the appearance information indicating the appearance may be referred to also as attention behavior information. The "behavior" in the attention behavior information may be regarded as static or dynamic state or response of a human or animal that can be observed objectively from the outside. The response can include a physiological phenomenon such as movement of the line of sight or the heartbeat.

For example, the appearance information is information indicating an attention frequency as the frequency of the user's paying attention to the object, information indicating the user's posture when the user is paying attention to the object, the biological information at a time when the user is paying attention to the object, a feature value based on the voice information when the user is paying attention to the object, or the like.

Next, the attention frequency will be described below. For example, when the object to which the user is paying attention is the floor number display, the identification unit 140 calculates the time for which the user pays attention to the floor number display or the number of times of paying attention to the floor number display in a predetermined time based on a plurality of images X2 including the user and identifies the attention frequency based on the result of the calculation.

The posture will be described below. The identification unit 140 identifies the user's posture when the user is paying attention to the object by using the image X2 including the user. Specifically, the identification unit 140 identifies the user's posture when the user is paying attention to the object based on the image X2 including the user and an image for identifying the posture. For example, when the image X2 indicates a state in which the user in an elevator hall is paying attention to the floor number display with crossed arms, the identification unit 140 identifies the crossed arms by performing template matching on the image X2 and an image indicating crossed arms. When posture information acquired from a posture detection sensor is included in the input information X1, the identification unit 140 identifies the posture based on the posture information indicating the posture of the user. When skeletal information on the user is included in the input information X1, the identification unit 140 identifies the posture based on the skeletal information. When the motion information is included in the input information X1, the identification unit 140 identifies the posture based on the motion information.

The biological information will be described below. The biological information is the biological information included in the input information X1. The biological information is a heart rate, a perspiration level or the like, for example.

The feature value based on the voice information will be described below. The feature value based on the voice information is a pitch, power, a spectrum or the like, for example. The feature value based on the voice information can also be the contents of the user's speech, for example.

As above, the identification unit 140 identifies the object to which the user is paying attention and the user's appearance when the user is paying attention. The object information indicating the identified object and the appearance information indicating the identified appearance are referred to as attention relevant information X4. Here, examples of the attention relevant information X4 will be described below.

FIG. 4 is a diagram showing examples of the attention relevant information in the first embodiment. The "attention target" indicated by the attention relevant information X4 in FIG. 4 represents the object to which the user is paying attention. Further, the "attention frequency", the "posture" and the "heart rate" indicated by the attention relevant information X4 in FIG. 4 represent the user's appearance when the user is paying attention. As shown in FIG. 4, a plurality of items of information indicating the user's appearance when the user is paying attention may be associated with the "attention target".

Further, a frame number may be associated with the "attention target" and the plurality of items of information. The frame number is the number of one frame or the number when a plurality of frames are regarded as one frame. For example, the "attention frequency", the "posture" and the "heart rate" when a plurality of frames are regarded as one frame indicate the "attention frequency", the "posture" and the "heart rate" at a predetermined time. Each of the "attention frequency" and the "heart rate" at a predetermined time can be a mean value, a maximum value, a minimum value or a representative value of values at predetermined times.

Incidentally, the step S14 may be executed before the step S13. Further, the step S14 may be executed in parallel with the step S13.

(Step S15) The acquisition unit 120 acquires the method table. When the method table has been stored in the storage unit 110, the acquisition unit 120 acquires the method table from the storage unit 110. The method table can also be stored in an external device connectable to the information processing device 100. When the method table has been stored in the external device, the acquisition unit 120 acquires the method table from the external device.

The method selection unit 150 selects a method to be used for estimating the emotion based on the attention relevant information X4 and the method table. As mentioned earlier, a plurality of methods have been registered in the method table. The plurality of methods will be described specifically below.

For example, a method of estimating the emotion by using an algebraic expression has been registered in the method table.

For example, a method of estimating the emotion by using a feature value and a threshold value used for judging the emotion has been registered in the method table. Further, a method of estimating that the emotion is irritation when the attention frequency is higher than or equal to 0.8 may be registered in the method table. Furthermore, a method of estimating that the emotion is normal when the heart rate is less than 60 may be registered in the method table.

For example, a method of estimating the emotion by assigning a weight to a feature value used for judging the emotion or a numerical value indicating the emotion has been registered in the method table. Incidentally, the numerical value indicating the emotion may be represented also as an importance level of emotion.

For example, a method of estimating the emotion by assigning a weight to an importance level of information indicated by the appearance information has been registered in the method table. Specifically, a method of estimating the emotion by assigning a weight to the "attention frequency" indicated by the appearance information has been registered in the method table.

For example, a method of estimating the emotion based on a predetermined rule has been registered in the method table. For example, a method of estimating the emotion by using a learned model or a method of estimating the emotion by using a classifier such as a Support Vector Machine (SVM) or a neural network has been registered in the method table. Here, a concrete example of the method table will be described below.

Figure 5:
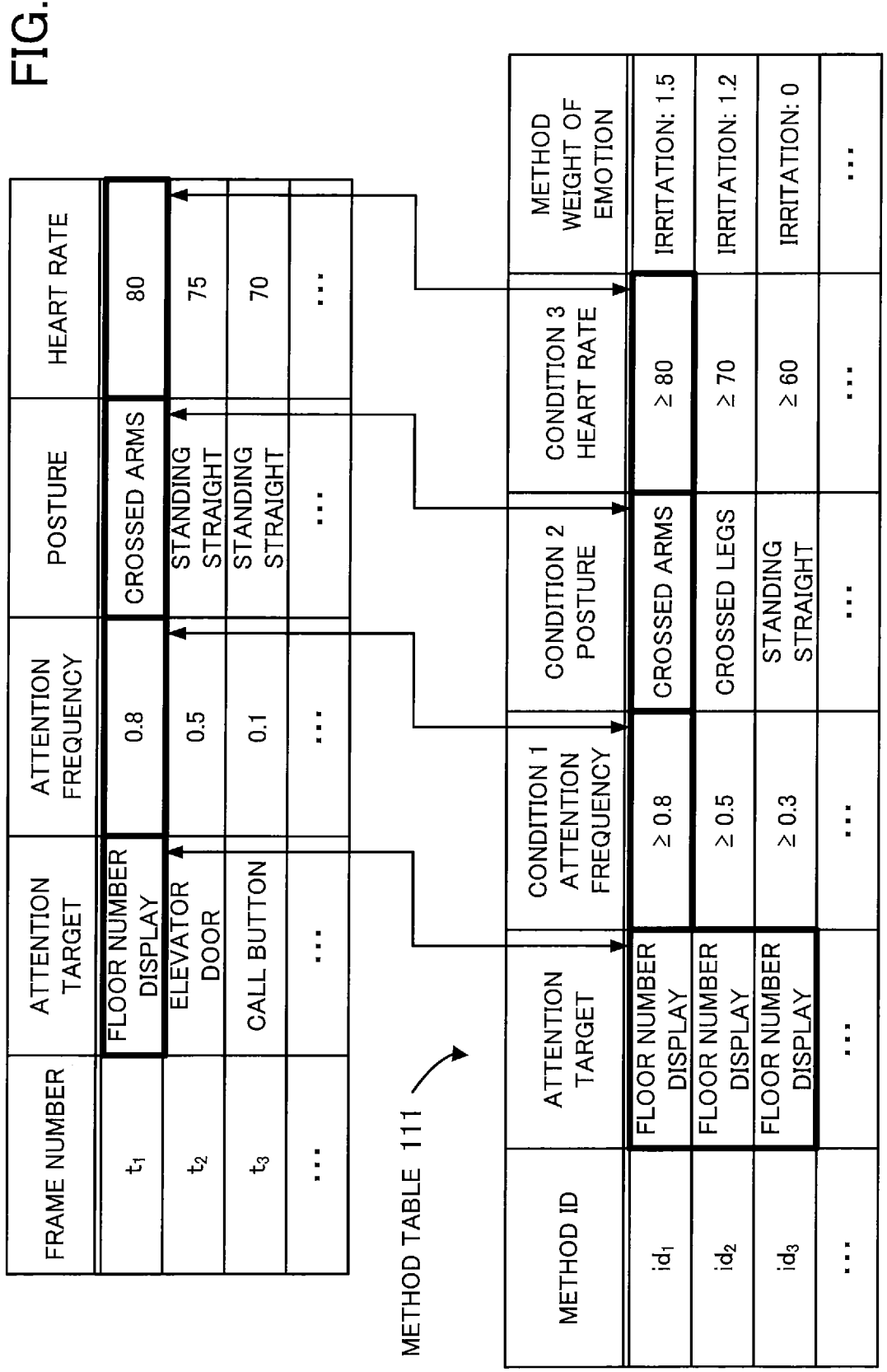
FIG. 5 is a diagram showing an example of a method table in the first embodiment.

FIG. 5 is a diagram showing an example of the method table in the first embodiment. For example, a method table 111 has been stored in the storage unit 110. The method table 111 includes items of a method ID, an attention target, a condition and a method. An identifier is registered in the item of the method ID. An object as the attention target is registered in the item of the attention target. A condition is registered in the item of the condition. In FIG. 5, items of three conditions are shown as an example. The number of items of conditions can also be one. Namely, the number of items of conditions is not limited to three. A method is registered in the item of the method. In the item of the method in FIG. 5, the method of estimating the emotion by assigning a weight to a feature value used for judging the emotion or a numerical value indicating the emotion has been registered.

For example, the method selection unit 150 searches the method table 111 for a record coinciding with conditions "floor number display" (attention target), "0.8" (attention frequency), "crossed arms" (posture) and "80" (heart rate) included in the attention relevant information X4. The method selection unit 150 selects a method of estimating the emotion by using "irritation: 1.5" as the weight and assigning the weight.

Further, when the emotion is the same and a plurality of weights are found by the search, the method selection unit 150 may use a value obtained by multiplying, adding or averaging the plurality of weights as the weight. The method selection unit 150 may also use a maximum value or a minimum value of the plurality of weights as the weight.

Information indicating the selected method is referred to as method information X5. The method information X5 can be a method ID indicating the selected method. Further, the method information X5 can be information as a combination of the attention target and the selected method. For example, the method information X5 can be information like "floor number display: irritation: 1.5".

(Step S16) The emotion estimation unit 160 estimates the emotion of the user based on the attention relevant information X4 and the method information X5. When the method ID is included in the method information X5, the emotion estimation unit 160 refers to the method table 111 and thereby identifies the method corresponding to the method ID. The emotion estimation unit 160 estimates the emotion of the user based on the identified method and the attention relevant information X4.

For example, when the weight used in the method indicated by the method information X5 is "irritation: 1.5" and the emotion estimated based on the attention relevant information X4 is "irritation", the emotion estimation unit 160 assigns the weight 1.5 to the value indicating "irritation".

For example, when the method information X5 indicates a method of estimating an emotion value by using a certain value, the emotion estimation unit 160 estimates the emotion value by using the attention relevant information X4 and the value.

For example, when the method information X5 indicates a method of estimating that the emotion is irritation when the attention frequency is higher than or equal to 0.8, the emotion estimation unit 160 estimates the emotion by comparing the attention frequency indicated by the attention relevant information X4 with "0.8".

Further, for example, the emotion estimation unit 160 estimates the emotion by using a rule, an algebraic expression, a learned model or a classifier used in the method indicated by the method information X5.

The emotion estimation unit 160 may change the weight or the threshold value used in the method indicated by the method information X5 and estimate the emotion by using the changed value.

The result of the estimation is referred to as result information X6. The result information X6 indicates delight, anger, sorrow, pleasure, fatigue, stress, the user's internal mood, or the like. Further, the result information X6 may indicate the emotion such as delight, anger, sorrow or pleasure by using a numerical value. The numerical value indicating the emotion is "delight: 0.5", for example. The emotion estimation unit 160 outputs the result information X6. For example, the emotion estimation unit 160 outputs the result information X6 to a display.

Furthermore, the emotion estimation unit 160 estimates the emotion in regard to each frame number. The emotion estimation unit 160 outputs a plurality of pieces of result information X6. When the plurality of pieces of result information X6 indicate numerical values, the emotion estimation unit 160 may output a maximum value. When the plurality of pieces of result information X6 indicate numerical values, the emotion estimation unit 160 may output the numerical value at a particular frame number as a representative value.

According to the first embodiment, the information processing device 100 estimates the emotion based on the attention relevant information X4. Specifically, the information processing device 100 estimates the emotion based on the object to which the user is paying attention and the user's appearance when the user is paying attention. Accordingly, the information processing device 100 is capable of increasing the estimation accuracy of the emotion.

Further, the information processing device 100 selects the method to be used for estimating the emotion from the method table 111 based on the attention relevant information X4. Namely, the information processing device 100 selects a method that is the most appropriate for estimating the emotion by using information indicated by the attention relevant information X4. Then, the information processing device 100 estimates the emotion by the selected method. Accordingly, the information processing device 100 is capable of realizing high-accuracy estimation.

The above description has been given of the case where the emotion estimation unit 160 estimates the emotion by using the selected method. The emotion estimation unit 160 may estimate the emotion of the user based on the object information, the appearance information and a predetermined method for estimating the emotion. The predetermined method is a method of estimating the emotion by using a threshold value or the method of estimating the emotion by assigning a weight to a feature value used for judging the emotion or a numerical value indicating the emotion, for example. Alternatively, the predetermined method is the method of estimating the emotion by using a rule, an algebraic expression, a learned model or a classifier such as an SVM, for example.

Second Embodiment

Next, a second embodiment will be described below. In the second embodiment, the description will be given mainly of features different from those in the first embodiment. In the second embodiment, the description is omitted for features in common with the first embodiment. FIGS. 1 to 5 are referred to in the description of the second embodiment.

Figure 6:
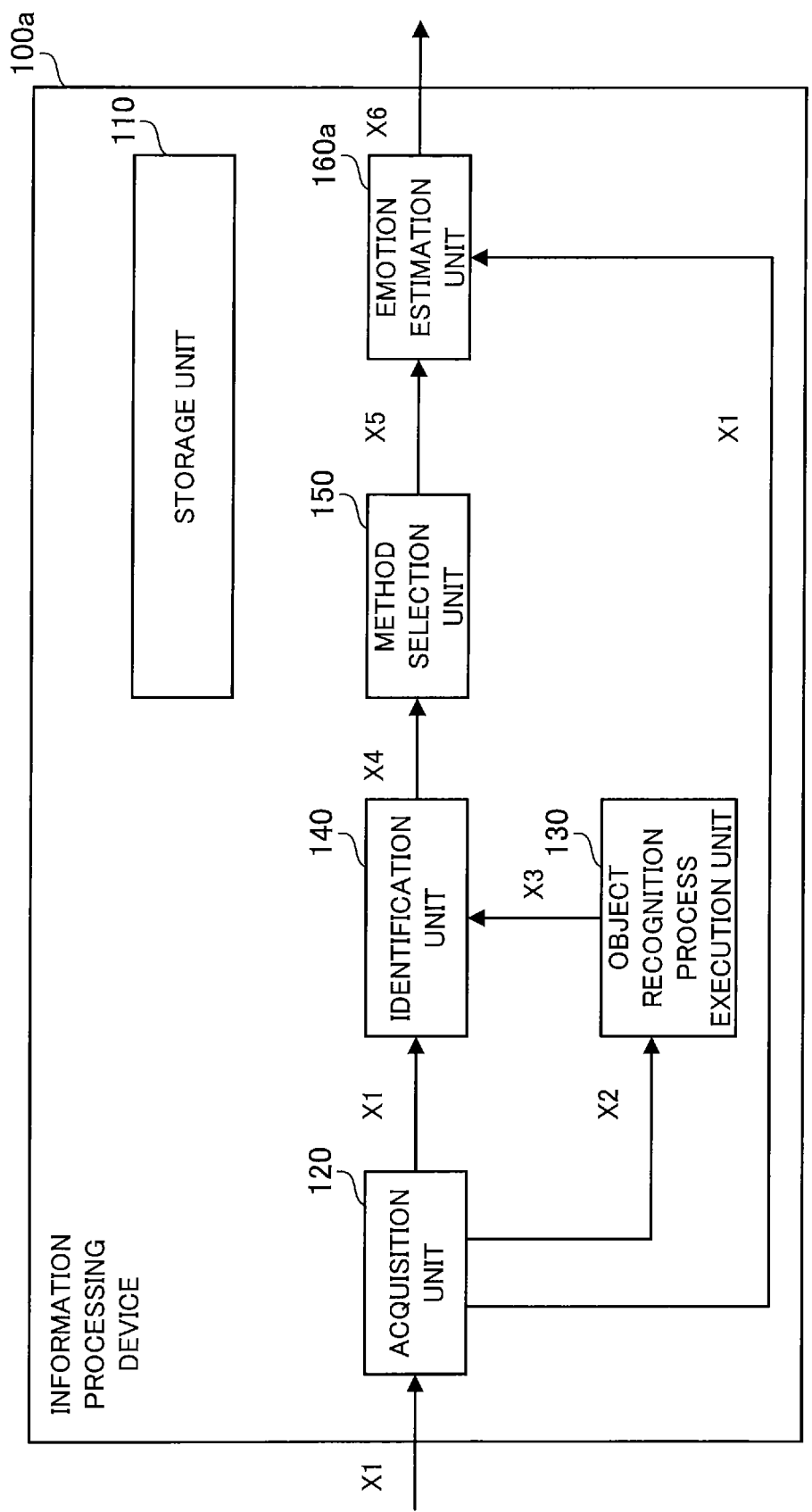
FIG. 6 is a diagram showing functional blocks included in an information processing device in a second embodiment.

FIG. 6 is a diagram showing functional blocks included in an information processing device in the second embodiment. Each component in FIG. 6 that is the same as a component shown in FIG. 1 is assigned the same reference character as in FIG. 1.

An information processing device 100a includes an emotion estimation unit 160a.

The acquisition unit 120 acquires the input information X1. The input information X1 is information regarding a user in a certain situation in a predetermined time period. Specifically, the input information X1 includes a plurality of images X2 obtained by photographing in the predetermined time period, voice information indicating voice of the user in the predetermined time period, biological information on the user in the predetermined time period, sight line data in the predetermined time period, motion information in the predetermined time period, or the like. In other words, the input information X1 is time-series data indicating feature values of the images X2, the voice information, the biological information, the sight line data, the motion information or the like.

The function of the emotion estimation unit 160a will be described later.

Next, a process executed by the information processing device 100a will be described below by using a flowchart.

Figure 7:
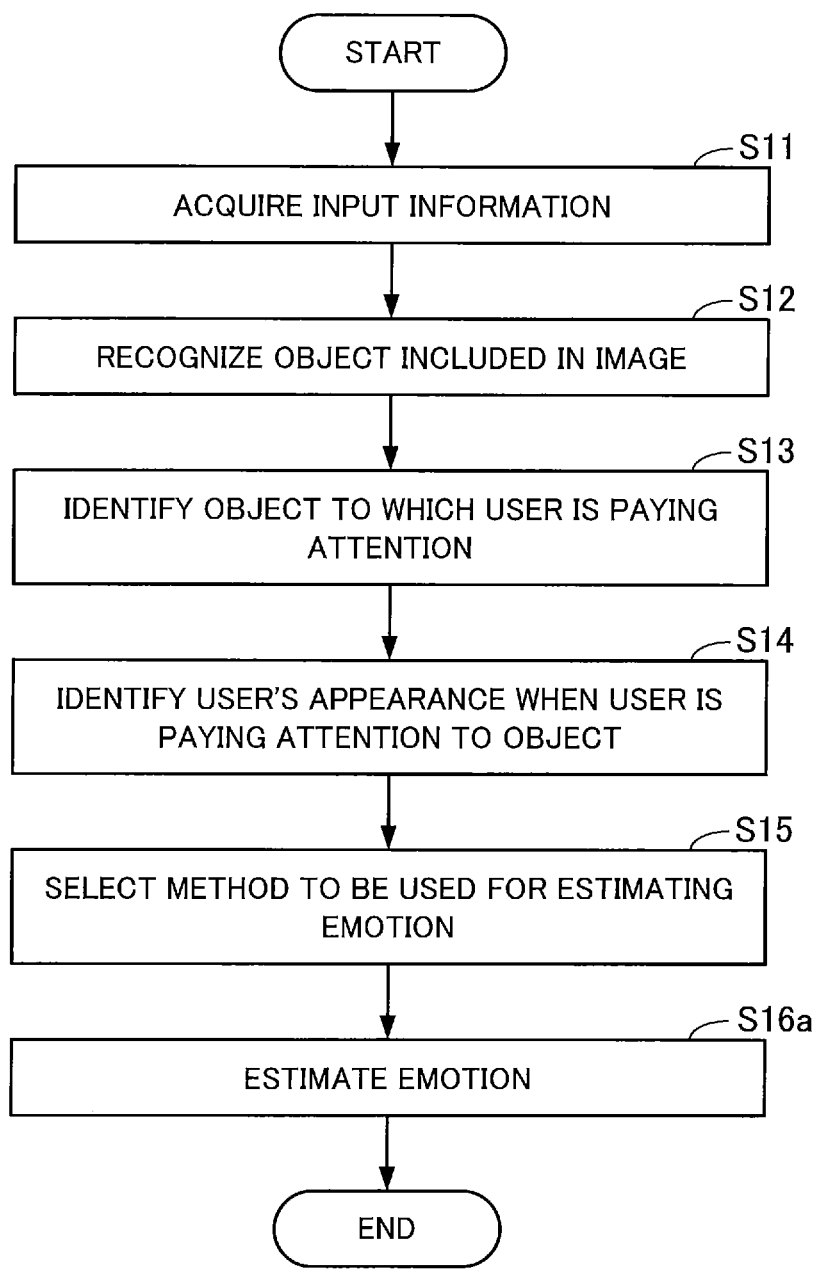
FIG. 7 is a flowchart showing an example of a process executed by the information processing device in the second embodiment.

FIG. 7 is a flowchart showing an example of the process executed by the information processing device in the second embodiment. The process of FIG. 7 differs from the process of FIG. 3 in that step S16a is executed. Thus, the step S16a will be described below with reference to FIG. 7. In regard to the other steps in FIG. 7, the description of the processing therein is left out by assigning them the same step numbers as in FIG. 3.

(Step S16a) The emotion estimation unit 160a estimates the emotion of the user based on the input information X1 and the method information X5. For example, when the method information X5 indicates a method of estimating the emotion by using a feature value and a predetermined threshold value, the emotion estimation unit 160a estimates the emotion based on the feature value indicated by the input information X1 and the threshold value. Further, for example, the emotion estimation unit 160a estimates the emotion by using a rule, an algebraic expression, a learned model or a classifier used in the method indicated by the method information X5.

The result of the estimation is referred to as the result information X6. The result information X6 indicates delight, anger, sorrow, pleasure, fatigue, stress, the user's internal mood, or the like. Further, the result information X6 may indicate the emotion such as delight, anger, sorrow or pleasure by using a numerical value. The emotion estimation unit 160a outputs the result information X6.

Incidentally, in the first embodiment, the emotion is estimated by using the attention relevant information X4. Namely, in the first embodiment, the emotion is estimated by using information at a time point when the user is paying attention. According to the second embodiment, the information processing device 100a estimates the emotion by using the input information X1. Therefore, the information processing device 100a is capable of estimating the emotion of the user in a predetermined time period.

Third Embodiment

Next, a third embodiment will be described below. In the third embodiment, the description will be given mainly of features different from those in the second embodiment. In the third embodiment, the description is omitted for features in common with the second embodiment. FIGS. 6 and 7 are referred to in the description of the third embodiment.

Figure 8:
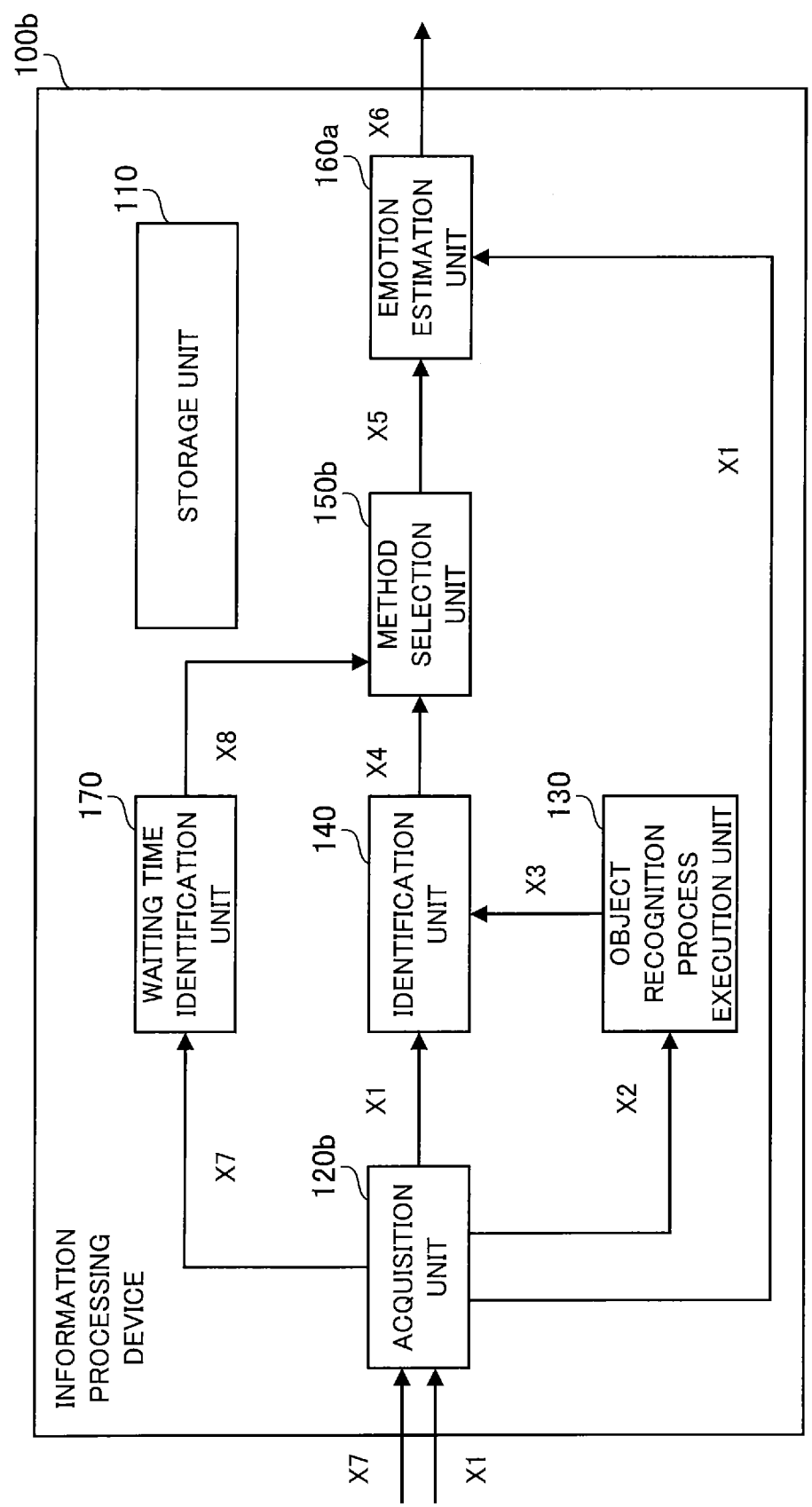
FIG. 8 is a diagram showing functional blocks included in an information processing device in a third embodiment.

FIG. 8 is a diagram showing functional blocks included in an information processing device in the third embodiment. Each component in FIG. 8 that is the same as a component shown in FIG. 6 is assigned the same reference character as in FIG. 6.

An information processing device 100b includes an acquisition unit 120b, a method selection unit 150b and a waiting time identification unit 170. Part or the whole of the waiting time identification unit 170 may be implemented by a processing circuitry. Part or the whole of the waiting time identification unit 170 may be implemented as a module of a program executed by the processor 101.

The acquisition unit 120b acquires the input information X1 and equipment information X7. The input information X1 is the input information X1 described in the second embodiment. The equipment information X7 is information regarding the equipment used by the user. For example, the equipment information X7 is time information regarding the time when a call button of an elevator was pressed, floor number display information on the elevator, information indicating the present position of the elevator car, or the like. Further, for example, the equipment information X7 is information indicating that a button of navigation equipment installed in a vehicle has been depressed, information regarding a screen displayed on the navigation equipment, information regarding voice guidance outputted by the navigation equipment, or the like.

Functions of the method selection unit 150b and the waiting time identification unit 170 will be described later.

Next, a process executed by the information processing device 100b will be described below by using a flowchart.

Figure 9:
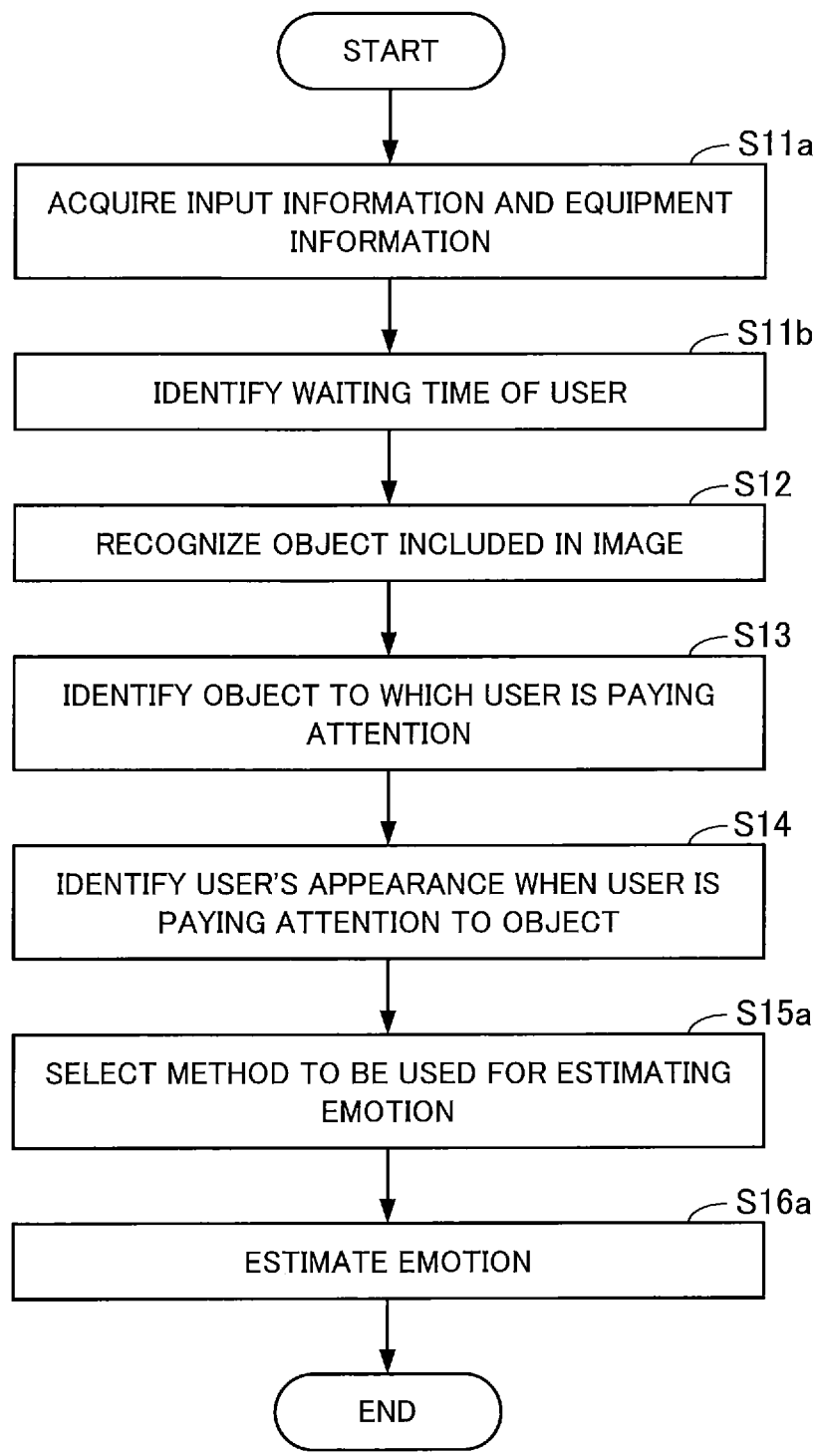
FIG. 9 is a flowchart showing an example of a process executed by the information processing device in the third embodiment.

FIG. 9 is a flowchart showing an example of the process executed by the information processing device in the third embodiment. The process of FIG. 9 differs from the process of FIG. 7 in that steps S11a, S11b and S15a are executed. Thus, the steps S11a, S11b and S15a will be described below with reference to FIG. 9. In regard to the other steps in FIG. 9, the description of the processing therein is left out by assigning them the same step numbers as in FIG. 7.

(Step S11a) The acquisition unit 120b acquires the input information X1 and the equipment information X7.

(Step S11b) The waiting time identification unit 170 identifies a time from the user's operation on the equipment to the return of a response to the operation as a waiting time based on the equipment information X7. The method of identifying the waiting time will be described specifically below.

For example, the equipment information X7 is assumed to include a depressing time as the time when the user depressed the call button of the elevator and a time when the elevator car arrived and the door opened. The waiting time identification unit 170 identifies the waiting time based on the depressing time and the time when the door opened. When the equipment information X7 does not include the time when the door opened, the waiting time identification unit 170 may identify the waiting time based on the depressing time and the time of day when the step S11b is executed (i.e., present time).

Further, for example, the equipment information X7 is assumed to include an operation time as the time when the navigation equipment was operated and an execution time as the time when the response to the operation was executed. The waiting time identification unit 170 identifies the waiting time based on the operation time and the execution time.

Furthermore, for example, the equipment information X7 is assumed to include an input time as the time when the voice information on voice uttered by the user was inputted to the navigation equipment and an execution time as the time when the response to the voice was executed. The waiting time identification unit 170 identifies the waiting time based on the input time and the execution time.

Information indicating the identified waiting time is referred to as "waiting time information X8". Further, the waiting time information X8 may be represented by the length of time. For example, the length of time is "long" or "short".

Incidentally, the step S11b may be executed anytime as long as it is before the step S15a is executed.

(Step S15a) The acquisition unit 120b acquires the method table 111. The method selection unit 150b selects the method to be used for estimating the emotion based on the attention relevant information X4, the waiting time information X8 and the method table 111. Specifically, based on the waiting time indicated by the waiting time information X8, the object information, the appearance information, and the method table 111, the method selection unit 150b selects a method corresponding to the waiting time, the object information and the appearance information from the plurality of methods indicated by the method table 111. Here, an example of the method table 111 will be described below.

Figure 10:
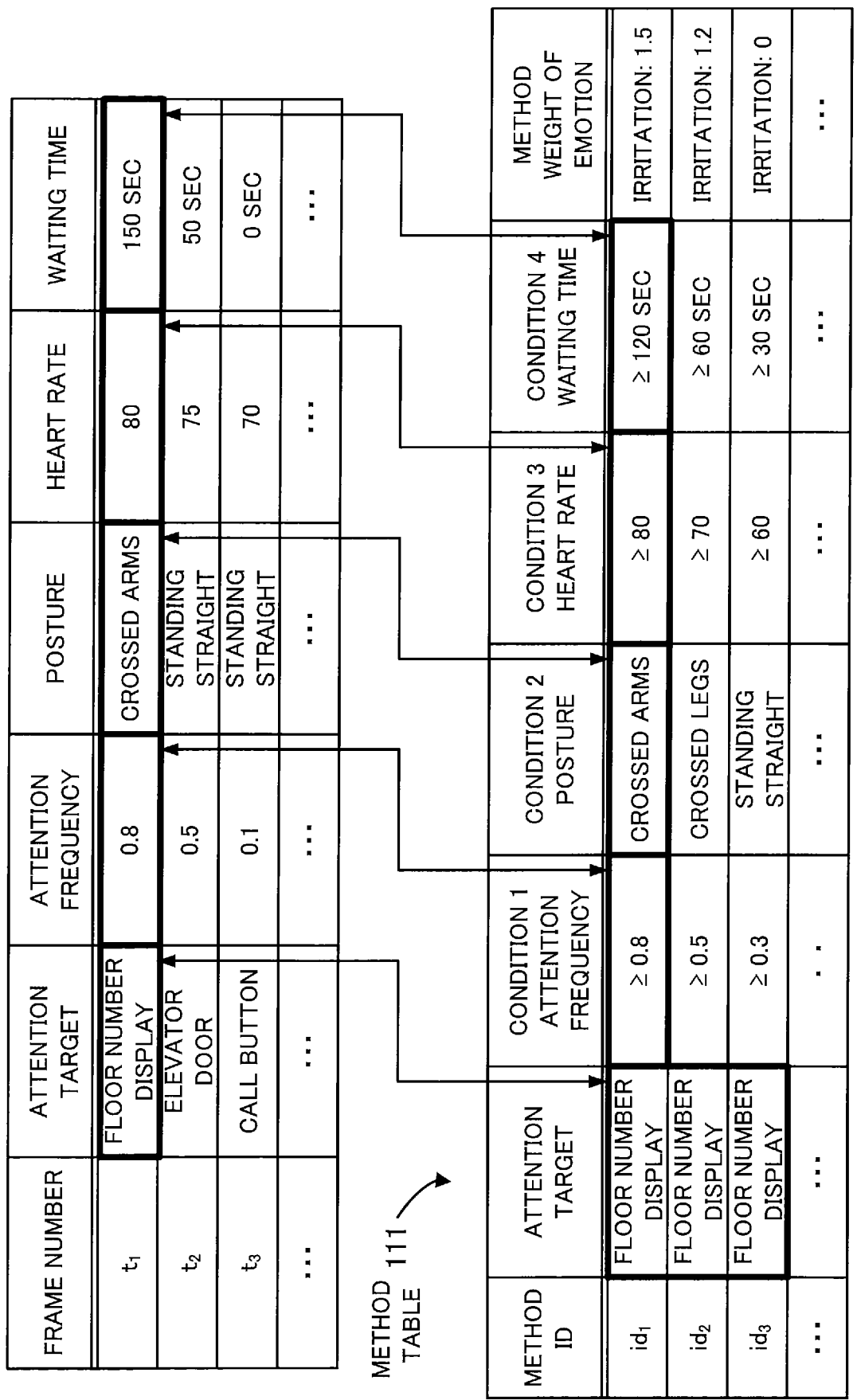
FIG. 10 is a diagram showing an example of a method table in the third embodiment.

FIG. 10 is a diagram showing an example of the method table in the third embodiment. FIG. 10 indicates that the method table 111 includes an item of a condition "waiting time".

For example, the method selection unit 150b searches the method table 111 for a record coinciding with conditions "floor number display" (attention target), "0.8" (attention frequency), "crossed arms" (posture) and "80" (heart rate) included in the attention relevant information X4 and "150 seconds" (waiting time) included in the waiting time information X8. The method selection unit 150b selects the method of estimating the emotion by using "irritation: 1.5" as the weight and assigning the weight.

Information indicating the selected method is referred to as the method information X5. The method information X5 can be a method ID indicating the selected method. Further, the method information X5 can be information as a combination of the attention target and the selected method. For example, the method information X5 can be information like "floor number display: irritation: 1.5".

According to the third embodiment, the information processing device 100b selects the method to be used for estimating the emotion from the method table 111 based on the attention relevant information X4 and the waiting time information X8. Namely, the information processing device 100b selects a method in consideration of the waiting time. Then, the information processing device 100b estimates the emotion by the selected method. Accordingly, the information processing device 100b is capable of realizing high-accuracy estimation.

Modification of Third Embodiment

In the third embodiment, the emotion estimation unit 160a estimates the emotion by the method selected by the method selection unit 150b. In a modification of the third embodiment, the emotion estimation unit 160 estimates the emotion by the method selected by the method selection unit 150b. Namely, in the modification of the third embodiment, the step S16 is executed after the step S15a.

According to the modification of the third embodiment, the information processing device 100b estimates the emotion based on the attention relevant information X4. Specifically, the information processing device 100b estimates the emotion based on the object to which the user is paying attention and the user's appearance when the user is paying attention. Accordingly, the information processing device 100b is capable of increasing the estimation accuracy of the emotion.

Further, the information processing device 100b selects the method to be used for estimating the emotion from the method table 111 based on the attention relevant information X4 and the waiting time information X8. Namely, the information processing device 100b selects a method in consideration of the waiting time. Then, the information processing device 100b estimates the emotion by the selected method. Accordingly, the information processing device 100b is capable of realizing high-accuracy estimation.

Fourth Embodiment

Next, a fourth embodiment will be described below. In the fourth embodiment, the description will be given mainly of features different from those in the second embodiment. In the fourth embodiment, the description is omitted for features in common with the second embodiment. FIGS. 6 and 7 are referred to in the description of the fourth embodiment.

Figure 11:
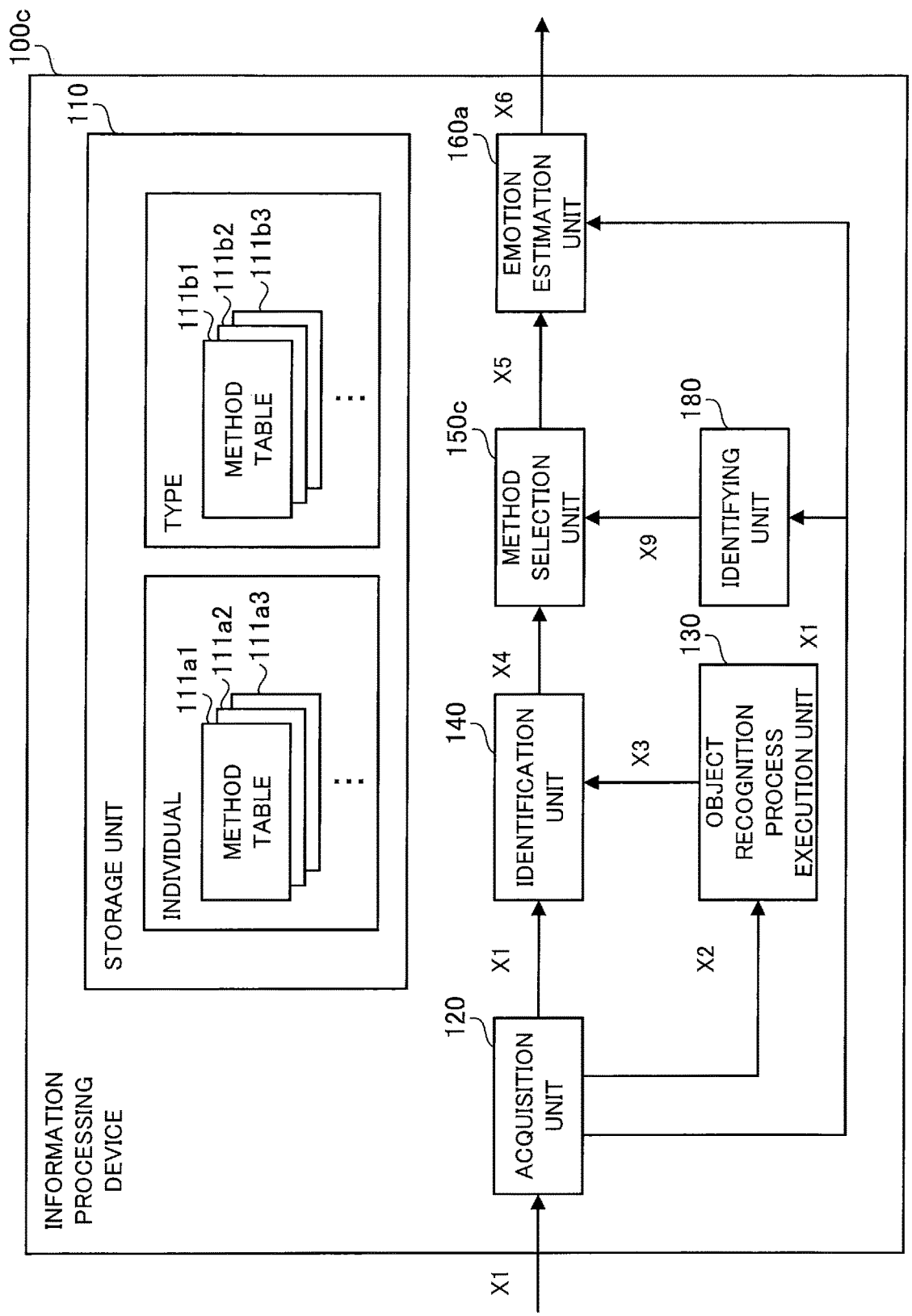
FIG. 11 is a diagram showing functional blocks included in an information processing device in a fourth embodiment.

FIG. 11 is a diagram showing functional blocks included in an information processing device in the fourth embodiment. Each component in FIG. 11 that is the same as a component shown in FIG. 6 is assigned the same reference character as in FIG. 6.

An information processing device 100c includes a method selection unit 150c and an identifying unit 180. Part or the whole of the identifying unit 180 may be implemented by a processing circuitry. Part or the whole of the identifying unit 180 may be implemented as a module of a program executed by the processor 101.

The storage unit 110 may store a plurality of method tables. The plurality of method tables will be described later.

The function of the method selection unit 150c will be described later.

The identifying unit 180 identifies at least one of the user or the type of the user based on the input information X1.

Next, a process executed by the information processing device 100c will be described below by using a flowchart.

FIG. 12 is a flowchart showing an example of the process executed by the information processing device in the fourth embodiment. The process of FIG. 12 differs from the process of FIG. 7 in that steps S11c and S15b are executed. Thus, the steps S11c and S15b will be described below with reference to FIG. 12. In regard to the other steps in FIG. 12, the description of the processing therein is left out by assigning them the same step numbers as in FIG. 7.

(Step S11c) The identifying unit 180 identifies at least one of the user or the type of the user based on the input information X1.

A method of identifying the user will be described concretely. For example, when an image X2 including the user is included in the input information X1, the identifying unit 180 identifies the user by using the image X2. Specifically, the identifying unit 180 identifies the user based on the image X2 and a publicly known technology. For example, the publicly known technology is generic object recognition or specific object recognition. Further, for example, when the motion information is included in the input information X1, the identifying unit 180 identifies the user based on the user's habit identified from the motion information. Specifically, the identifying unit 180 identifies the user based on a characteristic motion indicated by the motion information and information indicating a habit as a motion by which an individual can be identified. Incidentally, the information indicating the habit may be stored in the storage unit 110. Furthermore, for example, when the voice information is included in the input information X1, the identifying unit 180 identifies the user by using a feature value based on the voice information. Moreover, for example, when biological information regarding the heartbeat, an iris or a fingerprint is included in the input information X1, the identifying unit 180 identifies the user by using the biological information. Specifically, the identifying unit 180 identifies the user based on the biological information and a publicly known technology.

Next, a method of identifying the type will be described specifically below. For example, when one or more images X2 are included in the input information X1, the identifying unit 180 identifies the type of the user based on the user's facial expression indicated by the image(s) X2 or a change in the user's facial expression identified from a plurality of images X2. For example, the identified type is a short-tempered type, a gentle type or the like. Further, for example, when the motion information is included in the input information X1, the identifying unit 180 identifies the type of the user based on a characteristic motion indicated by the motion information. Furthermore, for example, when the voice information is included in the input information X1, the identifying unit 180 identifies the type of the user based on the way of speaking identified from the voice information. Moreover, for example, when the biological information is included in the input information X1, the identifying unit 180 identifies the type of the user based on the biological information. Specifically, the identifying unit 180 identifies the type of the user based on a feature value indicated by the biological information. For example, the identified type is a sweaty type or the like.

When user type information as information indicating the correspondence between users and types has been stored in the storage unit 110 or an external device and the user is identified, the identifying unit 180 may identify the type of the user based on the identified user and the user type information.

When information indicating at least one of the user and the type of the user is included in the input information X1, the identifying unit 180 identifies at least one of the user and the type of the user based on the information.

The identified information is referred to as identification information X9. The identification information X9 is information indicating at least one of the name and the type of the user. The identification information X9 can also be information indicating at least one of an ID of the identified user and an ID of the identified type.

Incidentally, the step S11c may be executed anytime as long as it is before the step S15b is executed.

(Step S15b) The acquisition unit 120 acquires a method table corresponding to the user or the type indicated by the identification information X9. The method table to be acquired has been stored in the storage unit 110 or an external device.

Here, a description will be given of a case where the method table to be acquired has been stored in the storage unit 110. For example, the storage unit 110 stores method tables 111a1 to 111a3 corresponding to individuals and method tables 111b1 to 111b3 corresponding to types.

For example, the acquisition unit 120 acquires the method table 111a1 corresponding to a user U1 indicated by the identification information X9 from the storage unit 110. Here, methods suitable for estimating the emotion of the user U1 have been registered in the item of the method in the method table 111a1. As above, methods suitable for estimating the emotion of a user indicated by the identification information X9 have been registered in each of the method tables 111a1 to 111a3.

Further, for example, the acquisition unit 120 acquires the method table 111b1 corresponding to a type TY1 indicated by the identification information X9 from the storage unit 110. Here, methods suitable for estimating the emotion of a user of the type TY1 have been registered in the item of the method in the method table 111b1. As above, methods suitable for estimating the emotion of a user of a type indicated by the identification information X9 have been registered in each of the method tables 111b1 to 111b3.

The method selection unit 150c selects the method to be used for estimating the emotion based on the attention relevant information X4 and the acquired method table. The processing of the selection is the same as the step S15 in the first embodiment. Thus, the description of the processing of the selection is left out.

When the identification information X9 is information indicating the user and the type, the following process is executed: The acquisition unit 120 acquires the method table 111. The method selection unit 150c selects the method to be used for estimating the emotion based on the attention relevant information X4, the identification information X9 and the method table 111. Here, an example of the method table 111 will be described below.

FIG. 13 is a diagram showing an example of the method table in the fourth embodiment. FIG. 13 indicates that the method table 111 includes an item of a condition "user" and an item of a condition "type".

For example, the method selection unit 150c searches the method table 111 for a record coinciding with conditions "floor number display" (attention target), "0.8" (attention frequency), "crossed arms" (posture) and "80" (heart rate) included in the attention relevant information X4 and "Usri" (user) and "short-tempered" (type) included in the identification information X9. The method selection unit 150c selects the method of estimating the emotion by using "irritation: 1.5" as the weight and assigning the weight.

Information indicating the selected method is referred to as the method information X5. The method information X5 can be a method ID indicating the selected method. Further, the method information X5 can be information as a combination of the attention target and the selected method. For example, the method information X5 can be information like "floor number display: irritation: 1.5".

According to the fourth embodiment, the information processing device 100c acquires a method table corresponding to the user indicated by the identification information X9 and thereby selects a method suitable for estimating the emotion of the user. Then, the information processing device 100c estimates the emotion by the selected method. Accordingly, the information processing device 100c is capable of realizing high-accuracy estimation. Further, the information processing device 100c acquires a method table corresponding to the type indicated by the identification information X9 and thereby selects a method suitable for estimating the emotion of a user of the type. Then, the information processing device 100c estimates the emotion by the selected method. Accordingly, the information processing device 100c is capable of realizing high-accuracy estimation.

Modification of Fourth Embodiment

In the fourth embodiment, the emotion estimation unit 160a estimates the emotion by the method selected by the method selection unit 150c. In a modification of the fourth embodiment, the emotion estimation unit 160 estimates the emotion by the method selected by the method selection unit 150c. Namely, in the modification of the fourth embodiment, the step S16 is executed after the step S15b.

According to the modification of the fourth embodiment, the information processing device 100c estimates the emotion based on the attention relevant information X4. Specifically, the information processing device 100c estimates the emotion based on the object to which the user is paying attention and the user's appearance when the user is paying attention. Accordingly, the information processing device 100c is capable of increasing the estimation accuracy of the emotion.

Further, the information processing device 100c acquires a method table corresponding to the user indicated by the identification information X9 and thereby selects a method suitable for estimating the emotion of the user. Then, the information processing device 100c estimates the emotion by the selected method. Accordingly, the information processing device 100c is capable of realizing high-accuracy estimation. Furthermore, the information processing device 100c acquires a method table corresponding to the type indicated by the identification information X9 and thereby selects a method suitable for estimating the emotion of a user of the type. Then, the information processing device 100c estimates the emotion by the selected method. Accordingly, the information processing device 100c is capable of realizing high-accuracy estimation.

Features in the embodiments described above can be appropriately combined with each other.

DESCRIPTION OF REFERENCE CHARACTERS 100, 100a, 100b, 100c: information processing device, 101: processor, 102: volatile storage device, 103: nonvolatile storage device, 104: input interface, 105: output interface, 110: storage unit, 111, 111a1-111a3, 111b1-111b3: method table, 120, 120b: acquisition unit, 130: object recognition process execution unit, 140: identification unit, 150, 150b, 150c: method selection unit, 160, 160a: emotion estimation unit, 170: waiting time identification unit, 180: identifying unit

What is claimed is:

1. An information processing device comprising:
   an acquiring circuitry to acquire input information as information regarding a user in a certain situation, method information indicating a plurality of methods, each of the plurality of methods being a method of estimating the emotion, and equipment information as information regarding equipment used by the user;
   an identification circuitry to identify an object to which the user is paying attention and the user's appearance when the user is paying attention to the object based on the input information;
   a waiting time identifying circuitry to identify a time from the user's operation on the equipment to a return of a response to the operation as a waiting time based on the equipment information;
   a method selecting circuitry to select a method among the plurality of methods corresponding to the waiting time, object information indicating the identified object, and appearance information indicating the identified appearance from the plurality of methods based on the waiting time, the object information, the appearance information and the method information; and
   an emotion estimating circuitry to estimate emotion of the user based on the selected method, the object information, and the appearance information; and
   output circuitry to output the estimated emotion to an external device or a display,
   wherein
   the input information includes at least one of an image obtained by photographing the user's vicinity, voice information indicating voice of the user, a plurality of images each including the user, posture information indicating the user's posture or skeletal information on the user, motion information indicating motion of the user, biological information at a time when the user is paying attention to the object, and sight line data indicating the user's attention position in the image, and
   the identification circuitry identifies the object to which the user is paying attention based on at least one of the image obtained by photographing the user's vicinity, the voice information indicating voice of the user, the plurality of images each including the user, the posture information indicating the user's posture or skeletal information on the user, the motion information indicating motion of the user, the biological information at the time when the user is paying attention to the object, and the sight line data.

2. The information processing device according to claim 1, further comprising an object recognition process executing circuitry, wherein
   the input information includes the image obtained by photographing the user's vicinity,
   the object recognition process executing circuitry executes a process of recognizing an object included in the image, and
   the identification circuitry identifies the object to which the user is paying attention based on information obtained by the process and the input information.

3. The information processing device according to claim 2, wherein the identification circuitry identifies the object to which the user is paying attention based on information obtained by the process and the image including the user.

4. The information processing device according to claim 2, wherein
   the input information includes the sight line data indicating the user's attention position in the image, and
   the identification circuitry identifies the object to which the user is paying attention based on information obtained by the process and the sight line data.

5. The information processing device according to claim 2, wherein
   the input information includes the motion information indicating motion of the user, and
   the identification circuitry identifies the object to which the user is paying attention based on information obtained by the process and the motion information.

6. The information processing device according to claim 1, wherein
   the input information includes the voice information indicating voice of the user, and
   the identification circuitry identifies the object to which the user is paying attention based on the voice information.

7. The information processing device according to claim 1, wherein
   the input information includes the plurality of images each including the user, and
   the identification circuitry identifies an attention frequency based on the plurality of images as the appearance, the attention frequency being a frequency of the user's paying attention to the object.

8. The information processing device according to claim 1, wherein
   the input information includes the image including the user, and
   the identification circuitry identifies the user's posture when the user is paying attention to the object by using the image as the appearance.

9. The information processing device according to claim 1, wherein
   the input information includes the posture information indicating the user's posture or skeletal information on the user, and
   the identification circuitry identifies the posture indicated by the posture information or a posture identified from the skeletal information as the appearance.

10. The information processing device according to claim 1, wherein
    the input information includes the biological information at a time when the user is paying attention to the object, and
    the appearance information is the biological information.

11. The information processing device according to claim 1, wherein
    the input information includes the voice information indicating voice of the user, and
    the appearance information is a feature value based on the voice information.

12. The information processing device according to claim 1, further comprising an identifying circuitry to identify the user based on the input information, wherein
    the acquiring circuitry acquires the method information corresponding to the user.

13. The information processing device according to claim 12, wherein
    the input information includes the image including the user, and
    the identifying circuitry identifies the user by using the image.

14. The information processing device according to claim 12, wherein
the input information includes the motion information indicating motion of the user, and
the identifying circuitry identifies the user based on the user's habit identified from the motion information.

15. The information processing device according to claim 12, wherein
the input information includes the voice information indicating voice of the user, and
the identifying circuitry identifies the user by using a feature value based on the voice information.

16. The information processing device according to claim 12, wherein
the input information includes the biological information on the user, and
the identifying circuitry identifies the user by using the biological information.

17. The information processing device according to claim 1, further comprising an identifying circuitry to identify a type of the user based on the input information, wherein
the acquiring circuitry acquires the method information corresponding to the type.

18. The information processing device according to claim 17, wherein
the input information includes the one or more images each including the user, and
the identifying circuitry identifies the type based on the user's facial expression or a change in the user's facial expression indicated by the one or more images.

19. The information processing device according to claim 17, wherein
the input information includes the motion information indicating motion of the user, and
the identifying circuitry identifies the type based on a characteristic motion indicated by the motion information.

20. The information processing device according to claim 17, wherein
the input information includes the voice information indicating voice of the user, and
the identifying circuitry identifies the type based on a way of speaking identified from the voice information.

21. The information processing device according to claim 17, wherein
the input information includes the biological information on the user, and
the identifying circuitry identifies the type by using the biological information.

22. An information processing device comprising:
an acquiring circuitry to acquire input information as information regarding a user in a certain situation in a predetermined time period, method information indicating a plurality of methods, the plurality of methods each being a method of estimating emotion, and equipment information as information regarding equipment used by the user;
an identification circuitry to identify an object to which the user is paying attention and the user's appearance when the user is paying attention to the object based on the input information;
a waiting time identifying circuitry to identify a time from the user's operation on the equipment to a return of a response to the operation as a waiting time based on the equipment information;
a method selecting circuitry to select a method among the plurality of methods corresponding to the waiting time, object information indicating the identified object, and appearance information indicating the identified appearance from the plurality of methods based on the waiting time, the object information, the appearance information and the method information; and
an emotion estimating circuitry to estimate the emotion of the user based on the selected method and the input information; and
output circuitry to output the estimated emotion to an external device or a display,
wherein
the input information includes at least one of an image obtained by photographing the user's vicinity, voice information indicating voice of the user, a plurality of images each including the user, posture information indicating the user's posture or skeletal information on the user, motion information indicating motion of the user, biological information at a time when the user is paying attention to the object, and sight line data indicating the user's attention position in the image, and
the identification circuitry identifies the object to which the user is paying attention based on at least one of the image obtained by photographing the user's vicinity, the voice information indicating voice of the user, the plurality of images each including the user, the posture information indicating the user's posture or skeletal information on the user, the motion information indicating motion of the user, the biological information at the time when the user is paying attention to the object, and the sight line data.

23. The information processing device according to claim 22, further comprising an identifying circuitry to identify the user based on the input information, wherein
the acquiring circuitry acquires the method information corresponding to the user.

24. The information processing device according to claim 22, further comprising an identifying circuitry to identify a type of the user based on the input information, wherein
the acquiring circuitry acquires the method information corresponding to the type.

25. An emotion estimation method performed by an information processing device, the emotion estimation method comprising:
acquiring input information as information regarding a user in a certain situation, method information indicating a plurality of methods, the plurality of methods each being a method of estimating the emotion, and equipment information as information regarding equipment used by the user, identifying an object to which the user is paying attention and the user's appearance when the user is paying attention to the object based on the input information, and identifying a time from the user's operation on the equipment to a return of a response to the operation as a waiting time based on the equipment information;
selecting a method among the plurality of methods corresponding to the waiting time, object information indicating the identified object, and appearance information indicating the identified appearance from the plurality of methods based on the waiting time, the object information, the appearance information and the method information; and
estimating emotion of the user based on the selected method, the object information, and the appearance information; and outputting the estimated emotion to an external device or a display, wherein the input information includes at least one of an image obtained by photographing the user's vicinity, voice information indicating voice of the user, a plurality of images each including the user, posture information indicating the user's posture or skeletal information on the user, motion information indicating motion of the user, biological information at a time when the user is paying attention to the object, and sight line data indicating the user's attention position in the image, and identifying the object to which the user is paying attention based on at least one of the image obtained by photographing the user's vicinity, the voice information indicating voice of the user, the plurality of images each including the user, the posture information indicating the user's posture or skeletal information on the user, the motion information indicating motion of the user, the biological information at the time when the user is paying attention to the object, and the sight line data.

26. An emotion estimation method performed by an information processing device, the emotion estimation method comprising:

acquiring input information as information regarding a user in a certain situation in a predetermined time period, method information indicating a plurality of methods, the plurality of methods each being a method of estimating emotion, and equipment information as information regarding equipment used by the user, identifying an object to which the user is paying attention and the user's appearance when the user is paying attention to the object based on the input information, and identifying a time from the user's operation on the equipment to a return of a response to the operation as a waiting time based on the equipment information;

selecting a method among the plurality of methods corresponding to the waiting time, object information indicating the identified object, and appearance information indicating the identified appearance from the plurality of methods based on the waiting time, the object information, the appearance information and the method information; and estimating the emotion of the user based on the selected method and the input information; and outputting the estimated emotion to an external device or a display, wherein the input information includes at least one of an image obtained by photographing the user's vicinity, voice information indicating voice of the user, a plurality of images each including the user, posture information indicating the user's posture or skeletal information on the user, motion information indicating motion of the user, biological information at a time when the user is paying attention to the object, and sight line data indicating the user's attention position in the image, and identifying the object to which the user is paying attention based on at least one of the image obtained by photographing the user's vicinity, the voice information indicating voice of the user, the plurality of images each including the user, the posture information indicating the user's posture or skeletal information on the user, the motion information indicating motion of the user, the biological information at the time when the user is paying attention to the object, and the sight line data.

27. An information processing device comprising:

a processor to execute a program; and a memory to store the program which, when executed by the processor, performs processes of, acquiring input information as information regarding a user in a certain situation, method information indicating a plurality of methods, the plurality of methods each being a method of estimating the emotion, and equipment information as information regarding equipment used by the user, identifying an object to which the user is paying attention and the user's appearance when the user is paying attention to the object based on the input information, and identifying a time from the user's operation on the equipment to a return of a response to the operation as a waiting time based on the equipment information;

selecting a method among the plurality of methods corresponding to the waiting time, object information indicating the identified object, and appearance information indicating the identified appearance from the plurality of methods based on the waiting time, the object information, the appearance information and the method information; and estimating emotion of the user based on the selected method, the object information, and the appearance information; and outputting circuitry to output the estimated emotion to an external device or a display, wherein the input information includes at least one of an image obtained by photographing the user's vicinity, voice information indicating voice of the user, a plurality of images each including the user, posture information indicating the user's posture or skeletal information on the user, motion information indicating motion of the user, biological information at a time when the user is paying attention to the object, and sight line data indicating the user's attention position in the image, and identifying the object to which the user is paying attention based on at least one of the image obtained by photographing the user's vicinity, the voice information indicating voice of the user, the plurality of images each including the user, the posture information indicating the user's posture or skeletal information on the user, the motion information indicating motion of the user, the biological information at the time when the user is paying attention to the object, and the sight line data.

28. An information processing device comprising:

a processor to execute a program; and a memory to store the program which, when executed by the processor, performs processes of, acquiring input information as information regarding a user in a certain situation in a predetermined time period, method information indicating a plurality of methods, the plurality of methods each being a method of estimating emotion, and equipment information as information regarding equipment used by the user, identifying an object to which the user is paying attention and the user's appearance when the user is paying attention to the object based on the input information, and identifying a time from the user's operation on the equipment to a return of a response to the operation as a waiting time based on the equipment information;

selecting a method among the plurality of methods corresponding to the waiting time, object information indicating the identified object, and appearance information indicating the identified appearance from the plurality of methods based on the waiting time, the object information, the appearance information and the method information; and estimating the emotion of the user based on the selected method and the input information; and outputting the estimated emotion to an external device or a display, wherein the input information includes at least one of an image obtained by photographing the user's vicinity, voice information indicating voice of the user, a plurality of images each including the user, posture information indicating the user's posture or skeletal information on the user, motion information indicating motion of the user, biological information at a time when the user is paying attention to the object, and sight line data indicating the user's attention position in the image, and identifying the object to which the user is paying attention based on at least one of the image obtained by photographing the user's vicinity, the voice information indicating voice of the user, the plurality of images each including the user, the posture information indicating the user's posture or skeletal information on the user, the motion information indicating motion of the user, the biological information at the time when the user is paying attention to the object, and the sight line data.

* * * * *